United States Patent [19]
Young et al.

[11] Patent Number: 5,531,724
[45] Date of Patent: Jul. 2, 1996

[54] FLUID CONTAINMENT BAG

[75] Inventors: Ruth E. Young; Daniel L. Young, both of Escondido; Richard E. Warrick, Encinitas; Clarence A. Cassidy; Terry H. Cassidy, both of Carlsbad, all of Calif.

[73] Assignee: American Innotek, Inc., San Marcos, Calif.

[21] Appl. No.: 296,187

[22] Filed: Aug. 29, 1994

Related U.S. Application Data

[60] Continuation-in-part of Ser. No. 865,454, Apr. 9, 1992, Pat. No. 5,354,132, which is a division of Ser. No. 657,354, Feb. 15, 1991, Pat. No. 5,116,139, which is a continuation-in-part of Ser. No. 404,734, Sep. 8, 1989, abandoned, which is a continuation-in-part of Ser. No. 3,848, Jan. 14, 1987, abandoned.

[51] Int. Cl.⁶ ..................................................... A61B 1/00
[52] U.S. Cl. .......................... 604/327; 604/351; 604/333
[58] Field of Search .................................. 604/351–353, 604/327–329, 333

[56] References Cited

U.S. PATENT DOCUMENTS

| | | |
|---|---|---|
| 1,123,951 | 1/1915 | Swanson . |
| 1,458,640 | 6/1923 | Chase . |
| 2,343,678 | 3/1944 | Larkin . |
| 2,640,484 | 6/1953 | Johnson . |
| 2,883,985 | 4/1959 | Evans . |
| 3,110,312 | 11/1963 | Wirth ...................................... 604/391 |
| 3,297,152 | 1/1967 | Corella et al. . |
| 3,331,421 | 7/1967 | Lambert . |
| 3,346,883 | 10/1967 | Ersek . |
| 3,366,116 | 1/1968 | Huck . |
| 3,403,715 | 10/1968 | Trudel . |
| 3,554,368 | 1/1971 | Nagel ...................................... 383/117 |
| 3,556,102 | 1/1971 | Davis . |
| 3,577,989 | 5/1971 | Anderson . |
| 3,597,770 | 8/1971 | Jacuzzi et al. . |
| 3,612,133 | 10/1971 | Jarund . |
| 3,797,734 | 3/1974 | Fleury et al. . |
| 3,865,165 | 2/1975 | Glass ........................................ 604/322 |
| 3,920,179 | 11/1975 | Hall . |
| 4,122,851 | 10/1978 | Grossner ................................. 604/353 |
| 4,173,979 | 11/1979 | Odis ........................................ 604/327 |
| 4,179,367 | 12/1979 | Barthell et al. . |
| 4,305,161 | 12/1981 | Diaz . |
| 4,387,713 | 6/1983 | Calanni . |

(List continued on next page.)

FOREIGN PATENT DOCUMENTS

| | | |
|---|---|---|
| 0263315 | 4/1988 | European Pat. Off. . |
| 1815038 | 7/1969 | Germany . |
| 2936622 | 3/1981 | Germany . |
| 2016929 | 9/1979 | United Kingdom . |
| 2094265 | 9/1982 | United Kingdom . |
| 2227728 | 8/1990 | United Kingdom . |

OTHER PUBLICATIONS

Elias, *Mega Molecules* (1985), pp. 155–163, Springer–Verlag New York, N.Y.
"Sporty's" Catalogue (1989) p. 65.
"Introducing Restop" Brochure (1985)—4 pages.
Hoechst Celanse, "Sanwet Superabsorbent Polymers" (Date Unknown), 5 pp.
Sunrise Medical, "No More Dirty Work" (1989), 4 pp.

*Primary Examiner*—Randall L. Green
*Assistant Examiner*—Mark O. Polutta
*Attorney, Agent, or Firm*—Brown, Martin, Haller & McClain

[57] ABSTRACT

A containment and disposal system for human bodily fluids includes a bag and a holster that allows a user to quickly and easily remove and replace the bag. The bag includes an envelope having a hollow interior, an opening for receiving the bodily fluids from a catheter via a one-way valve, and hydrophilic material within the bag that rapidly gels bodily fluids in the bag upon contact. Prior to and during gellation, the one-way valve inhibits escape of the bodily fluids. The gellation sequesters the bodily fluids, and the gelled material further facilitates closure of the one-way valve. The hydrophilic material may include a polymer that is activated upon contact with the bodily fluids.

3 Claims, 2 Drawing Sheets

U.S. PATENT DOCUMENTS

| | | | |
|---|---|---|---|
| 4,435,171 | 3/1984 | Goldberg et al. | 604/326 |
| 4,490,145 | 12/1984 | Campbell | 604/333 |
| 4,511,358 | 4/1985 | Johnson et al. | 604/327 |
| 4,581,763 | 1/1986 | Olsen | 383/49 |
| 4,790,834 | 12/1988 | Austin | 604/349 |
| 4,820,291 | 4/1989 | Terauchi et al. | 604/349 |
| 5,002,986 | 3/1991 | Fujiura et al. | 524/47 |
| 5,032,118 | 7/1991 | Mason | 604/349 |
| 5,067,821 | 11/1991 | Young | 383/36 |
| 5,193,553 | 3/1993 | Kalinoski | 128/767 |
| 5,234,419 | 8/1993 | Bryant et al. | 604/320 |
| 5,267,989 | 12/1993 | Moyet-Ortiz | 604/349 |
| 5,307,819 | 5/1994 | Trautmann et al. | 128/767 |
| 5,315,960 | 5/1994 | Lamp | 119/95 |
| 5,404,999 | 4/1995 | Bednar | 206/204 |
| 5,409,474 | 4/1995 | Fleeman-Hardwick | 604/349 |

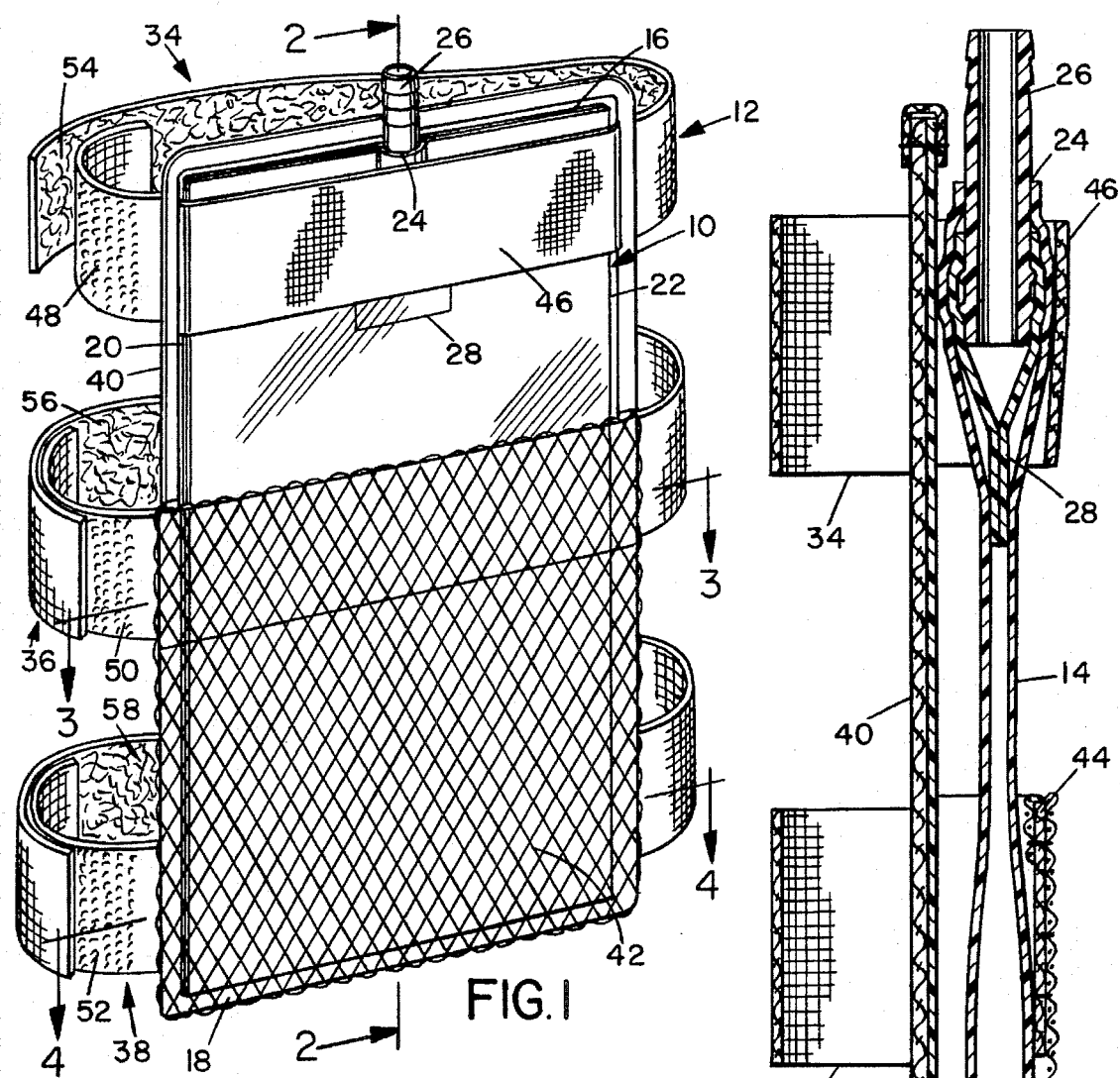
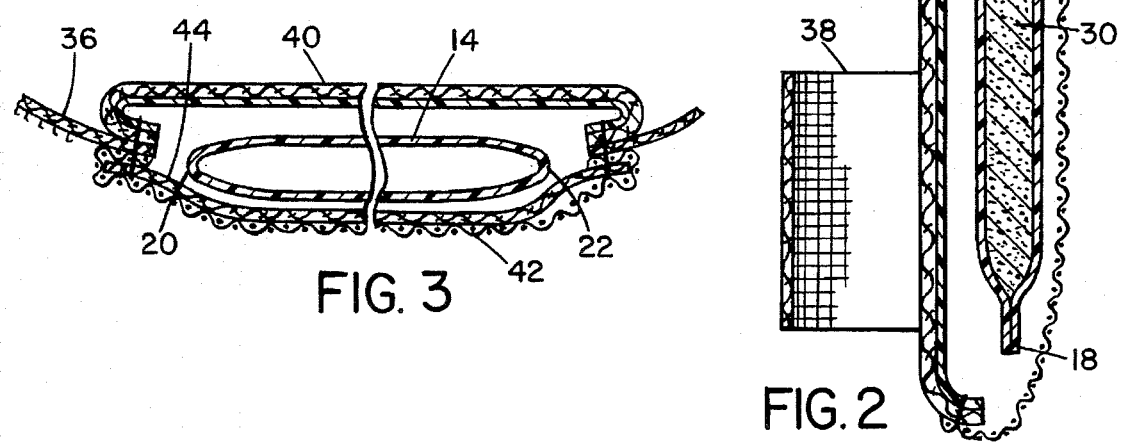

FLUID CONTAINMENT BAG

CROSS-REFERENCES TO RELATED APPLICATIONS

This application is a continuation-in-part of application Ser. No. 07/865,454, filed Apr. 9, 1992 now U.S. Pat. No. 5,354,132, which is a division of application Ser. No. 07/657,354, filed Feb. 15, 1991, now U.S. Pat. No. 5,116,139, which, is a continuation-in-part of Ser No. 07/404,734, filed Sep. 8, 1989, now abandoned, which is a continuation-in-part of application Ser. No. 07/003,848, filed on Jan. 14, 1987, now abandoned.

BACKGROUND OF THE INVENTION

1. Field of the Invention

The present invention relates generally to fluid containment bags and, more specifically, to a disposable bag for collection and containment of human bodily fluids such as urine, feces, or bile via a catheter.

2. Description of the Related Art

Persons who have undergone a colostomy, ileostomy or other surgical procedure involving the digestive tract may use a bag connected via a catheter or other connecting device to the stoma for collecting the effluent. Similarly, incontinent persons may use a bag connected via a catheter to their urinary tracts. Such bags typically have a flattened, rectangular shape with an opening in the top edge for receiving the fluid. The bag may also include an opening with a controllable valve in the bottom edge for periodically draining the fluid that collects in the bag.

The bag may be secured to the person's leg and concealed beneath clothing while the person moves about or may be suspended from a support while the person sleeps. The bag may include straps for securing it to a person's leg. The straps are typically made of an elastomeric material and looped through slits near the top and bottom edges of the bag. The straps known in the art are uncomfortable because they tend to bind the wearer's skin or leg hair when they are adjusted during attachment and removal. Moreover, the straps are cumbersome to adjust when the person desires to remove the bag. The wearer may attach a tube to the drain valve and use it to direct the stream of draining fluid into a toilet for disposal.

Practitioners in the art have recognized several problems associated with bodily fluid collection bags. Fluid may slosh about in the bag and annoy or embarrass the wearer. In addition, fluid in the bag may backflow into the catheter, increasing the risk of infecting the wearer. Punctures as small as a pinhole can cause fluid to leak. Furthermore, odors can escape through the same path along which fluid can backflow or through a puncture. Even the plastic walls of certain bags are not sufficiently impermeable to odors to completely prevent their escape.

U.S. Pat. No. 4,179,367, issued to Barthell et al., describes a hydrophilic polymer in granular or powdered form that forms a stiff gel or semisolid when it mixes with a water-based fluid such as urine collected in a bag. Mixing the polymer with collected urine thus prevents it from sloshing. Perfumes may be mixed with the hydrophilic polymer to mask odors.

Gelling a bodily fluid as suggested by Barthell et al. necessarily precludes draining it from the bag. Such a bag could not be emptied and must be discarded when the polymer is exhausted. Such a bag would thus be disposable, in contrast to a conventional re-usable or drainable fluid collection bag. The need to remove and replace a disposable fluid collection bag would arise much more frequently than the need to remove and replace a drainable fluid collection bag. It would therefore be desirable to provide a means for allowing a wearer to quickly and easily remove and replace a disposable bag.

A fluid collection bag having a gellable polymer, as suggested by Barthell et al., would be as susceptible to the same backflow problem as a conventional drainable fluid collection bag. The gelled material has a curd-like consistency that is considerably more viscous than bodily fluids and thus does not slosh about. Nevertheless, the gelled material would be undesirably expelled from such a bag if the bag were upset or squeezed.

Practitioners in the art have developed drainable fluid collection bags that include a one-way valve at the intake opening to reduce backflow of collected fluids into the catheter if the bag is upset or squeezed. The one-way valve may consist of a pliable tube that extends into the bag from the intake opening. The tube has a flattened shape when empty of fluid because it has two opposing walls that meet along two seams. Fluid may enter the bag because its pressure spreads apart the opposing walls of the tube. Fluid that has thus collected in the bag closes the valve by exerting pressure on the external walls of the tube, thereby forcing them together. The tube remains closed until further fluid is introduced. This type of one-way valve is often called a "flutter valve." Examples of bodily fluid collection bags having flutter valves are disclosed in U.S. Pat. Nos. 2,883,985, issued to Evans, U.S. Pat. No. 3,331,421, issued to Lambert, U.S. Pat. No. 3,403,410, issued to Benzel, et al., and U.S. Pat. No. 4,581,763, issued to Olsen. The perimeters of the walls of a flutter valve may, in the closed position, define a rectangular or ribbon shape, such as those disclosed by Olsen and Evans, or a triangular or conical shape, such as those disclosed by Lambert and Benzel, et al. Flutter valves may reduce fluid backflow, but the sealing effect is rather poor and does not completely prevent backflow. Flutter valves may also allow gases and their associated odor to escape.

These problems and deficiencies are clearly felt in the art and are solved by the present invention in the manner described below.

SUMMARY OF THE INVENTION

The present invention comprises a disposable bag for collecting bodily fluids and a holster for removably securing the bag to a wearer's body. The bag comprises an envelope with an opening for receiving bodily fluids, a one-way valve in fluid communication with the opening for preventing backflow of the fluids through the opening, and a hydrophilic material within the envelope that can gel water-based fluids. The envelope is a bag-like structure having any suitable shape and formed in any suitable manner. The hydrophilic material gels the bodily fluids rapidly upon contact when the bodily fluids are introduced into the bag.

The fluid may enter the bag through a catheter attached to the bag at its opening. As used herein, "catheter" refers to any suitable connecting tube or device for introducing fluid into the bag.

The one-way valve opens in response to entry of fluid into it and closes in response to the backflow of fluid or gelled material that has passed through it. The one-way valve may comprise a flutter valve, which is disposed at least partially within the envelope. The gel improves the operation of the flutter valve over flutter valves actuated by liquid alone by maintaining the valve more securely in a closed position. The relatively dense gel presses the flutter valve walls together or against the inside surface of the envelope. The cooperation of the gelled material and the flutter valve completely sequesters the material in the bag.

The hydrophilic material may comprise a polymer. The envelope may contain a mixture, including the hydrophilic material and other materials, such as enzymes, deodorants, fragrances, or human body abnormality indicators and/or pregnancy indicators. The material may be in any of a variety of physical forms, such as powder, granules, fibers, mats or foam.

The fluid collection bag of the present invention is preferably not reusable and must be discarded when all of the gellable material has been gelled. The need to remove and replace the bag may thus arise quite frequently. The present invention includes a convenient holster that is secured to a person's leg using straps. A wearer can quickly and easily remove the used bag from the holster for disposal and slip a fresh bag into the holster. Both the body of the holster and the straps are made of a soft fabric material that is comfortable against the wearer's skin. Although the holster particularly facilitates the use of the disposable bag of the present invention, it may also be used with conventional, drainable bags by providing a lower opening in the body of the holster to accommodate the drain tube.

The straps of the holster may have VELCRO®-type hook-and-loop fasteners to facilitate adjustment of their length around the wearer's leg. The soft, pile-like loop material of the fasteners may be disposed on essentially the entire inside surface of the strap both to provide a comfortable feel against the wearer's skin and to provide maximal strap length adjustability. The body of the holster has a pocket that securely retains the bag but allows the wearer to quickly and easily withdraw and remove the bag for disposal. The pocket may include elastic material for resiliently retaining the bag. The pocket may comprise a mesh or other see-through material to allow a wearer to visually inspect the contents of the bag. A wearer can thus determine when he must replace the bag.

The foregoing, together with other features and advantages of the present invention, will become more apparent when referring to the following specification, claims, and accompanying drawings.

BRIEF DESCRIPTION OF THE DRAWINGS

For a more complete understanding of the present invention, reference is now made to the following detailed description of the embodiments illustrated in the accompanying drawings, wherein:

FIG. 1 is a perspective view of the fluid containment bag and holster;

FIG. 2 is an enlarged sectional view taken on line 2—2 of FIG. 1;

FIG. 3 is an enlarged sectional view taken on line 3—3 of FIG. 1;

DESCRIPTION OF THE PREFERRED EMBODIMENTS

Figure 4:
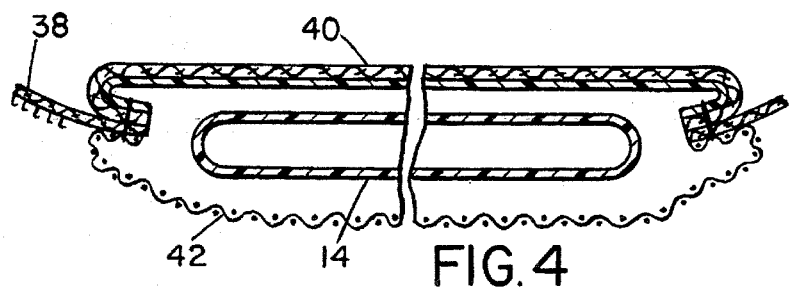
FIG. 4 is an enlarged sectional view taken on line 4—4 of FIG. 1.

As illustrated in FIGS. 1–3, the system comprises a fluid containment bag 10 and a leg holster 12. Bag 10 comprises an envelope 14, which is preferably constructed of a lightweight flexible plastic material that is fluid-impermeable, such as polyethylene, co-polymer vinyl, mylar, or the like, and that is sufficiently thick and resilient to resist accidental puncture under normal handling. Envelope 14 preferably has a generally rectangular perimeter defined by upper and lower edges 16 and 18, respectively, and side edges 20 and 22. Envelope 14 is preferably transparent to allow a person to gauge the amount of fluid collected in the bag. The plastic material of envelope 14 is preferably tubing that is heat-sealed to form upper and lower edges 16 and 18. Upper edge 16 has an opening 24 in which is disposed a barbed connector 26 for attaching a catheter, shown in phantom line in FIG. 5. In other embodiments, the envelope may be formed of two sheets of plastic material that are sealed along all four edges or of a single sheet of plastic material that is folded over on itself and sealed. Envelope 14 preferably has a capacity to hold on the order of between ten to twenty fluid ounces (300–600 cc) of bodily fluids.

Figure 5:
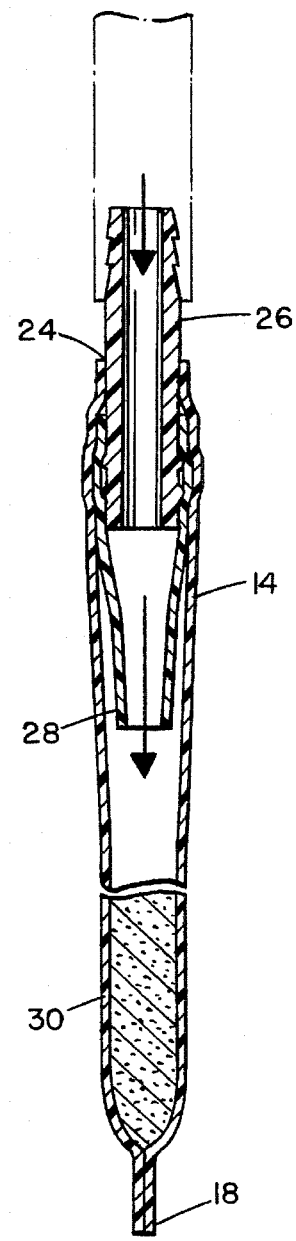
FIG. 5 is a sectional view of the bag as shown in FIG. 1, with the flutter valve open to admit fluid.
Figure 6:
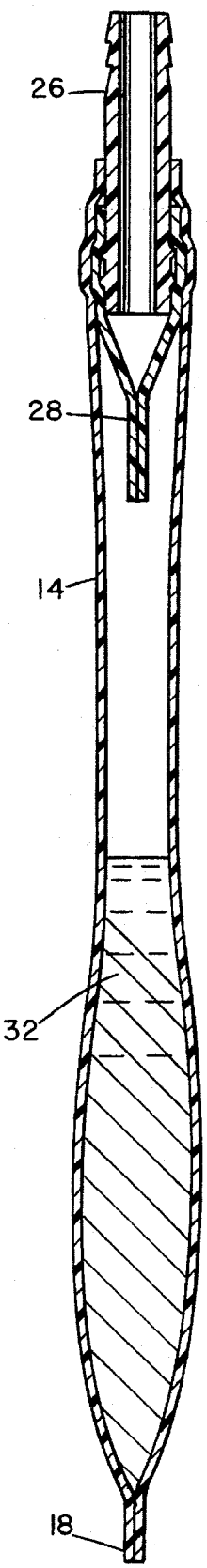
FIG. 6 is a similar sectional view of the bag, with the flutter valve closed and the fluid gelling in response to contact with the gellable material.

A flutter valve 28 inside envelope 14 is connected to the lower end of connector 26. Flutter valve 28 comprises a tube of flexible plastic material that assumes a flattened or ribbon-like shape when in the closed position. As shown in FIG. 5, when fluid enters flutter valve 28 through connector 26, the opposing walls spread open to admit the fluid in response to pressure exerted on the internal surfaces of the walls. As shown in FIG. 6, when all fluid has exited flutter valve 28, the opposing walls close in response to the resiliency of the opposing walls. In the closed position, opposing walls of flutter valve 28 are in contact with each other, thereby preventing fluid in envelope 14 from re-entering connector 26. Furthermore, the pressure exerted on the flutter valve by the fluid itself maintains it in the closed position.

As shown in FIG. 2, enclosed within envelope 14 and critical to the function of the present invention is a quantity of a gellable material 30 for transforming the fluid entering the bag into a gelatinous or semi-solid state. Gellable material 30 contains a hydrophilic polymer that gels very rapidly (normally within 30 seconds, and often much less than that) upon contact with water-based liquids. Such polymers are commercially available and are commonly found in a variety of known products, including disposable diapers and cleaning compositions. Typical examples include the acrylonitrile-based polymers described in Elias, *Mega Molecules*, pp. 157–158 (1987) and the acrylic polymers described in U.S. Pat. No. 4,179,367. Gellable material 30 is preferably a complex mixture including not only the polymer but also a material such as a protease enzyme to attack and break down the urine, blood or other bodily fluid. Deodorants, fragrances, biocides, antiviral substances, dyes, pregnancy indicators and human abnormality indicators may also be included in gellable material 30. These materials may formulated in any suitable "time release" manner known in the art to delay their activation or to spread their activation over a period of time. Gellable material 30 may be in any convenient physical form that can be placed into envelope 14; granular, powdered, foamed, matted, woven and fibrous forms are all suitable. The inventors of the present invention have successfully used a granular material commercially available under the trade name "Sanwet IM-5600" from Hoechst Celanese, Superabsorbent Material Division, of Portsmouth, Va. which is described as containing a starch grafted sodium polyacrylate. This product is a proprietary product and the exact identification of the components and formula is not available to the inventors of the present invention. In tests, the product has shown the property of gelling and sequestering all bodily fluids placed into test bags within no more than twenty seconds.

The particle sizes of the granulated material can be within a fairly wide range, but preferably will have at least about 80%, more preferably 80%–90%, in the range of −40+120 mesh U.S. Sieve Series (74–240 μm). It has been found that within this range, and more preferably with at least about 50% in the range of −40+80 mesh (177–240 μm), the liquid absorbency rate is maximized. If a large proportion of the granules are smaller than 120 mesh, there will be a tendency for the material to dust unduly in handling and storage prior to use and to restrict liquid flow throughout the material during use, while if there is a large proportion with particle sizes larger than 40 mesh, the rate of liquid absorption will be slowed. A typical analysis will be 8%+40 mesh, 66% −40+80 mesh, 19% −80+120 mesh and 7%−120 mesh.

When fluid enters envelope 14, flutter valve 28 not only immediately prevents it from flowing back into connector 26, but it thereafter prevents the gelled material 32 from flowing back into connector 26, as shown in FIG. 6. Flutter valve 28 thus performs two sequential functions to essentially completely prevent fluid from escaping envelope 14. The likelihood of gelled material 32 escaping is minimized because gelled material 32 is too viscous or dense to penetrate the closed lower end of flutter valve 28. Moreover, when the bag is upset, the shifting gelled material 32 tends to press flutter valve 28 against the wall of envelope 14 to a greater extent than a liquid.

Because bag 10 is disposable, there is a need to remove and replace it relatively frequently. A person may wear bag 10 in holster 12, which the person attaches to his leg. Holster 12 has three straps 34, 36 and 38 made of an elasticized fabric material. Holster 12 has a pocket defined by a backing panel 40 attached to three edges of a netting or mesh panel 42 using suitable stitching. The upper portion of mesh panel 42 is reinforced with a length of elasticized material 44, which also facilitates retention of bag 10 in the pocket. A similar elasticized strap 46 retains the upper portion of bag 10 in the pocket.

A person may attach holster 12 to his leg using straps 34, 36 and 38. Each of straps 34–38 has a VELCRO®-like fastener, consisting of respective hook portions 48, 50 and 52 and respective loop portions 54, 56 and 58. The person may easily adjust the length of straps 34–38 by engaging the corresponding hook and loop portions at the desired point along their lengths. Although hook portions 48–52 may be relatively small in area, loop portions 54–58 preferably cover essentially the entire inside surfaces of straps 34–38, respectively. The relatively large area covered by loop portions 54–58 both maximizes adjustability and provides a soft surface against the person's skin.

A person may easily insert bag 10 into the pocket of holster 12 and attach a catheter to connector 26. As with conventional bodily fluid collection bags, the person may move about with the bag attached to his leg and concealed beneath his clothing. Backing panel 40 is made of a soft fabric and is substantially coextensive with the dimensions of bag 10, thereby protecting the person's skin against irritation as a result of contact with bag 10. Mesh panel 42 expands to accommodate the expansion of bag 10 as it fills with fluid. The person can view the contents of bag 10 through mesh panel 42 or can remove bag 10 from holster 12 to gauge whether bag 10 is sufficiently full that it must be discarded. If bag 10 is full, the person can quickly and easily replace it with a new bag 10.

Holster 12 may, in other embodiments, have an opening (not shown) in its lower edge to accommodate a drain valve of a re-usable bag (not shown). A person may drain the bag more easily than conventional bags having cumbersome integral straps by simply removing it from holster 12, draining it, and replacing it in holster 12.

It will be evident that there are numerous embodiments of the present invention which, not specifically described above, are clearly within the scope and spirit of the invention. Consequently, the above description is considered to be exemplary only and the full scope of the invention is to be determined solely by the appended claims.

What is claimed is:

1. A method for sequestering a fluid in a bag, comprising the steps of:

receiving said fluid into an envelope through a one-way valve, said envelope containing a hydrophilic material, said fluid contacting said hydrophilic material;

closing said one-way valve in response to contact between said one-way valve and said fluid in said envelope to prevent escape of said fluid from said envelope;

gelling said fluid to form a gelled material in response to contact between said fluid and said hydrophilic material; and closing said one-way valve in response to contact between said one-way valve and said gelled material in said envelope to prevent escape of said gelled material from said envelope.

2. The method for sequestering a fluid in a bag a claimed in claim 1, wherein:

said one-way valve comprises a flutter valve having a flattened pliable portion extending from said opening into said interior of said envelope;

said step of closing said one-way valve in response to contact between said one-way valve and said fluid in said envelope comprises the step of contacting said fluid with said flattened pliable portion; and said step of closing said one-way valve in response to contact between said one-way valve and said gelled material in said envelope comprises the step of contacting said gelled material with said flattened pliable portion.

3. The method for sequestering a fluid in a bag as claimed in claim 2, wherein:

said gellable hydrophilic material comprises a polymer; and said step of gelling said fluid to form a gelled material comprises the step of contacting said fluid with said polymer.

\* \* \* \* \*